(12) United States Patent
Lane et al.

(10) Patent No.: US 7,648,497 B2
(45) Date of Patent: Jan. 19, 2010

(54) ENDOVASCULAR CRYOTREATMENT CATHETER

(75) Inventors: Miriam Lane, Ste-Anne de Bellevue (CA); Leonilda Capuano, Montréal (CA); David Holtan, Beaconsfield (CA); Jean-Pierre Lalonde, Verdun (CA); Claudia Lückge, L'Ile Berrot (CA); Jean-Luc Pageard, Montréal (CA); Marwan Abboud, Pierrefonds (CA); Johnny Al Asmar, Montréal (CA); Abderrahim Benrabah, Pointe-Claire (CA); Ken Chen, West Vancouver (CA); John W. Lehmann, Wayland, MA (US); Philippe Marchand, Hudson (CA); Robert Martin, Poughkeepsie, NY (US); Fredric L. Milder, Brookline, MA (US); Daniel Nahon, Ottawa (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 509 days.

(21) Appl. No.: 11/244,710

(22) Filed: Oct. 6, 2005

(65) Prior Publication Data

US 2006/0030843 A1    Feb. 9, 2006

Related U.S. Application Data

(60) Division of application No. 10/397,619, filed on Mar. 26, 2003, now Pat. No. 7,300,433, which is a continuation of application No. 09/945,319, filed on Aug. 31, 2001, now Pat. No. 6,575,966, which is a continuation-in-part of application No. 09/378,972, filed on Aug. 23, 1999, now Pat. No. 6,283,959.

(51) Int. Cl.
*A61B 18/18* (2006.01)
(52) U.S. Cl. ......................................... 606/21; 606/23
(58) Field of Classification Search .............. 606/20–26
See application file for complete search history.

(56) References Cited

U.S. PATENT DOCUMENTS

| 4,952,357 A | 8/1990 | Euteneuer |
| 5,160,321 A | 11/1992 | Sahota et al. |
| 5,246,421 A | 9/1993 | Saab |

(Continued)

FOREIGN PATENT DOCUMENTS

WO    WO 99/27862    6/1999

(Continued)

*Primary Examiner*—Michael Peffley
(74) *Attorney, Agent, or Firm*—Christopher & Weisberg, P.A.

(57) ABSTRACT

An elongated catheter device with a distal balloon assembly is adapted for endovascular insertion. Coolant injected through the device may, in different embodiments, directly cool tissue contacting the balloon, or may cool a separate internal chamber. In the first case, the coolant also inflates the balloon, and spent coolant is returned to the handle via a return passage extending through the body of the catheter. Plural balloons may be provided, wherein a secondary outer balloon surrounds a primary inner balloon, the primary balloon being filled with coolant and acting as the cooling chamber, the secondary balloon being coupled to a vacuum return lumen to serve as a robust leak containment device and thermal insulator around the cooling chamber. Various configurations, such as surface modification of the balloon interface, or placement of particles, coatings, or expandable meshes or coils in the balloon interface, may be employed to achieve this function.

15 Claims, 9 Drawing Sheets

U.S. PATENT DOCUMENTS

| | | | |
|---|---|---|---|
| 5,273,526 A | 12/1993 | Dance et al. | |
| 5,484,385 A | 1/1996 | Rishon | |
| 5,487,385 A | 1/1996 | Avitall | |
| 5,575,766 A | 11/1996 | Swartz et al. | |
| 5,632,762 A | 5/1997 | Myler | |
| 5,673,695 A | 10/1997 | McGee et al. | |
| 5,725,521 A | 3/1998 | Mueller | |
| 5,776,129 A | 7/1998 | Mersch | |
| 5,827,273 A | 10/1998 | Edwards | |
| 5,860,970 A * | 1/1999 | Goddard et al. | 606/23 |
| 5,860,971 A | 1/1999 | Clarke | |
| 5,868,735 A | 2/1999 | Lafontaine | |
| 5,899,899 A | 5/1999 | Arless et al. | |
| 5,902,299 A | 5/1999 | Jayaraman | |
| 5,938,660 A | 8/1999 | Swartz et al. | |
| 5,964,778 A | 10/1999 | Fugoso et al. | |
| 5,971,979 A | 10/1999 | Joye et al. | |
| 5,980,486 A | 11/1999 | Enger | |
| 5,992,158 A | 11/1999 | Goddard et al. | |
| 6,012,457 A | 1/2000 | Lesh | |
| 6,024,740 A | 2/2000 | Lesh et al. | |
| 6,036,697 A | 3/2000 | DiCaprio | |
| 6,042,559 A | 3/2000 | Dobak, III et al. | |
| 6,090,083 A | 7/2000 | Sell et al. | |
| 6,106,518 A | 8/2000 | Wittenberger et al. | |
| 6,120,477 A | 9/2000 | Campbell et al. | |
| 6,161,543 A | 12/2000 | Cox et al. | |
| 6,164,283 A | 12/2000 | Lesh | |
| 6,179,827 B1 | 1/2001 | Davis | |
| 6,214,002 B1 | 4/2001 | Fleischman et al. | |
| 6,233,491 B1 | 5/2001 | Kordis et al. | |
| 6,241,754 B1 | 6/2001 | Swanson et al. | |
| 6,245,064 B1 | 6/2001 | Lesh | |
| 6,270,493 B1 * | 8/2001 | Lalonde et al. | 606/23 |
| 6,290,696 B1 | 9/2001 | Lafontaine | |
| 6,305,378 B1 | 10/2001 | Lesh | |
| 6,325,797 B1 | 12/2001 | Stewart et al. | |
| 6,355,029 B1 * | 3/2002 | Joye et al. | 606/21 |
| 6,416,511 B1 | 7/2002 | Lesh et al. | |
| 6,440,126 B1 * | 8/2002 | Abboud et al. | 606/22 |
| 6,471,694 B1 | 10/2002 | Kudaravalli et al. | |
| 6,502,576 B1 | 1/2003 | Lesh | |
| 6,514,245 B1 * | 2/2003 | Williams et al. | 606/21 |
| 6,648,878 B2 | 11/2003 | Lafontaine | |
| 6,648,879 B2 | 11/2003 | Joye et al. | |
| 6,652,515 B1 | 11/2003 | Maguire et al. | |
| 6,685,732 B2 | 2/2004 | Kramer | |
| 6,989,009 B2 | 1/2006 | Lafontaine | |
| 2001/0005791 A1 | 6/2001 | Ginsburg et al. | |

FOREIGN PATENT DOCUMENTS

| | | |
|---|---|---|
| WO | WO 00/47118 | 8/2000 |

* cited by examiner

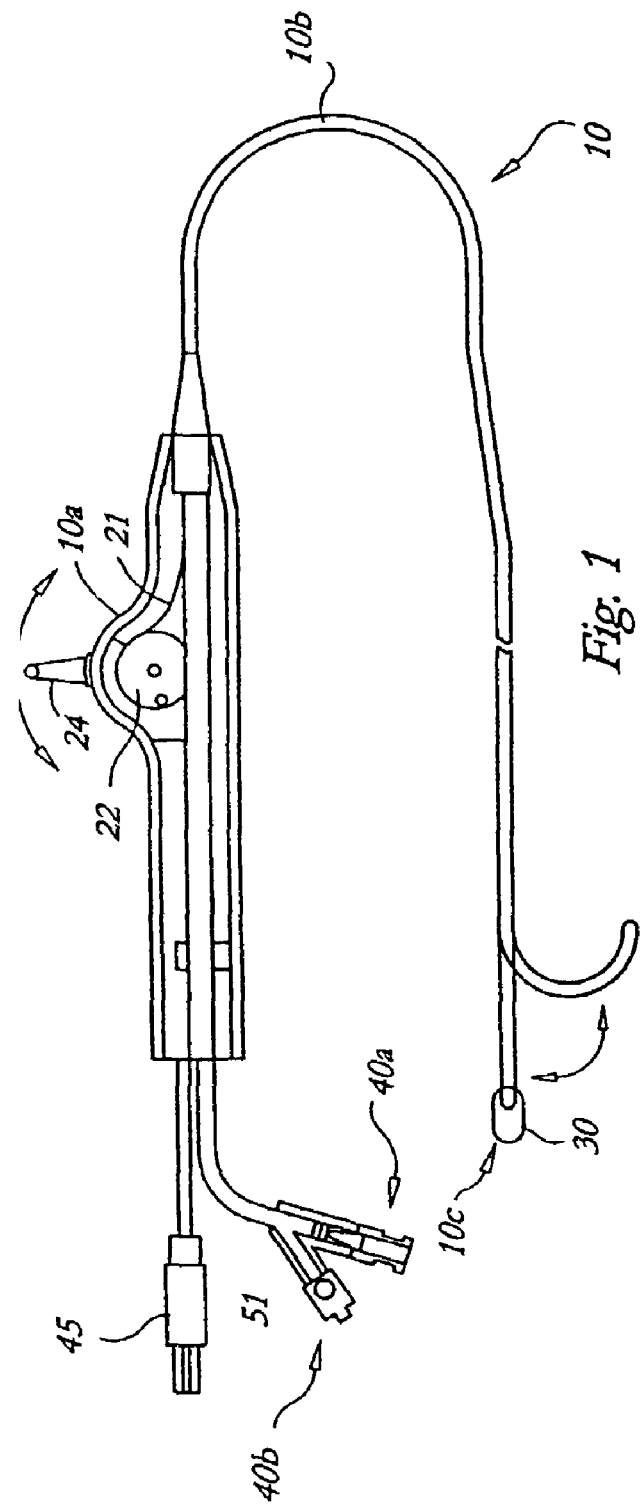
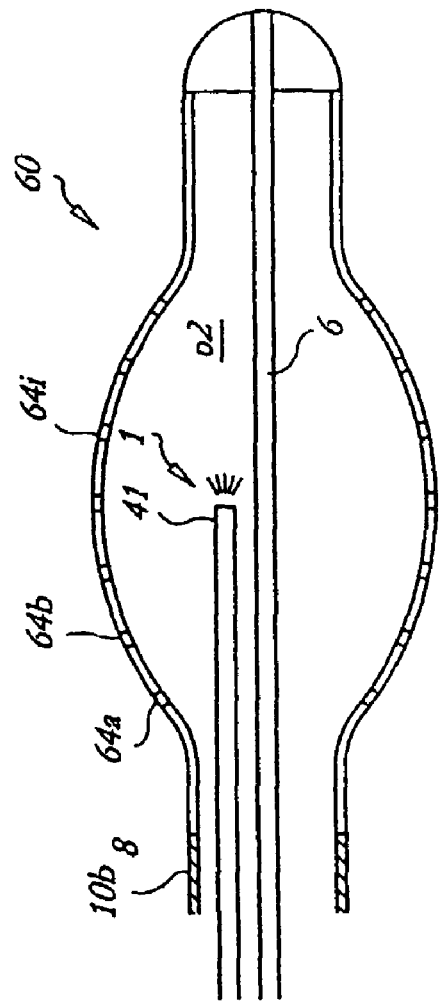
Fig. 1
Fig. 2

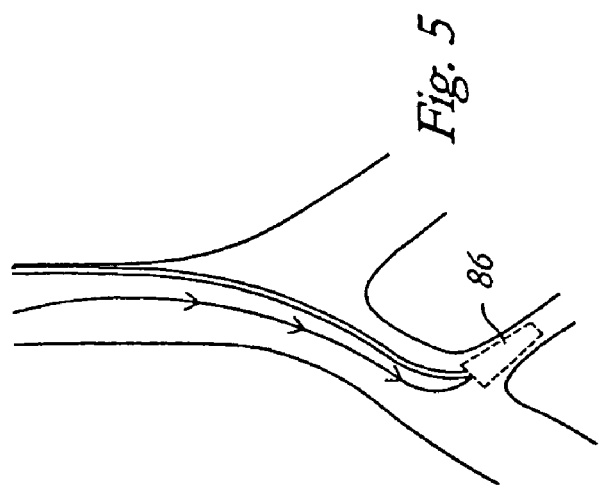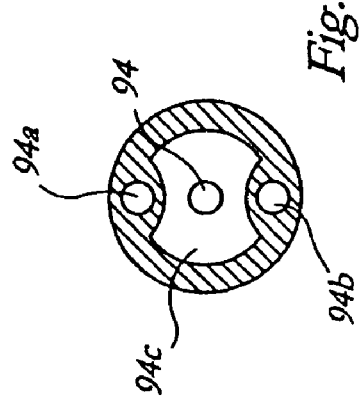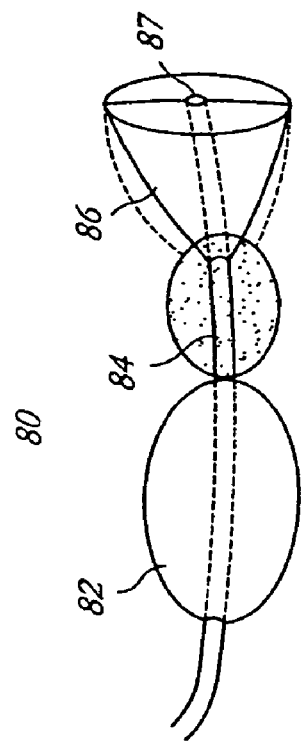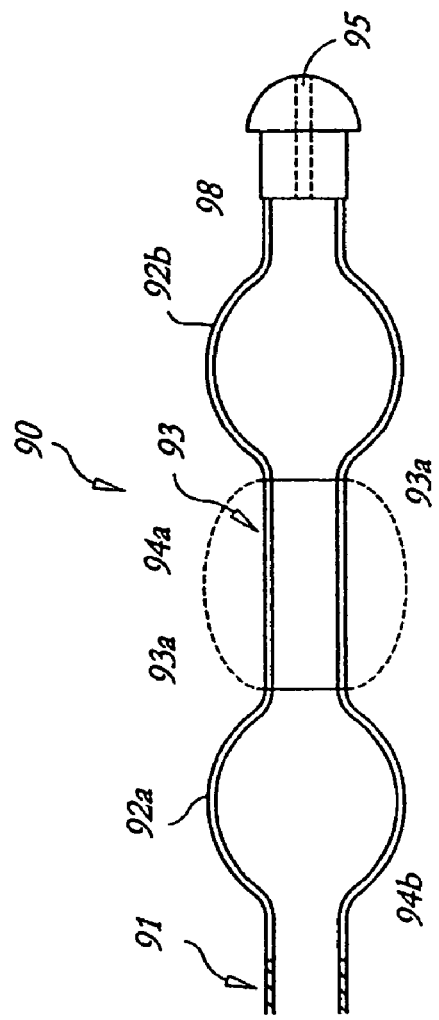

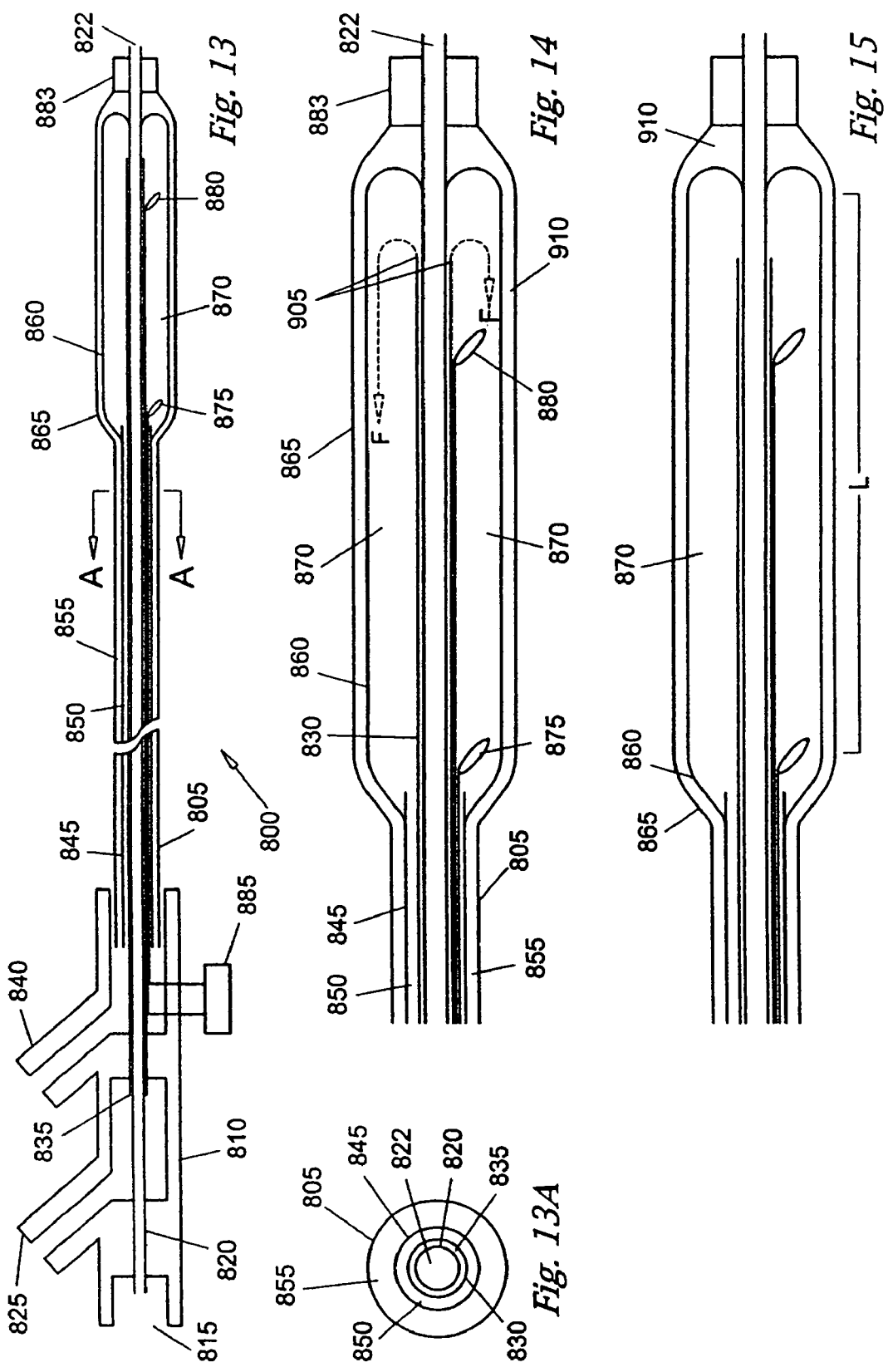

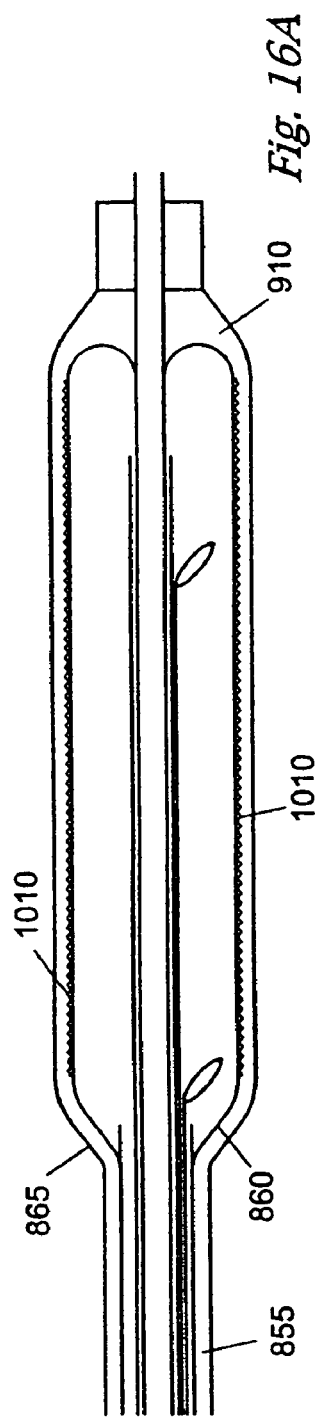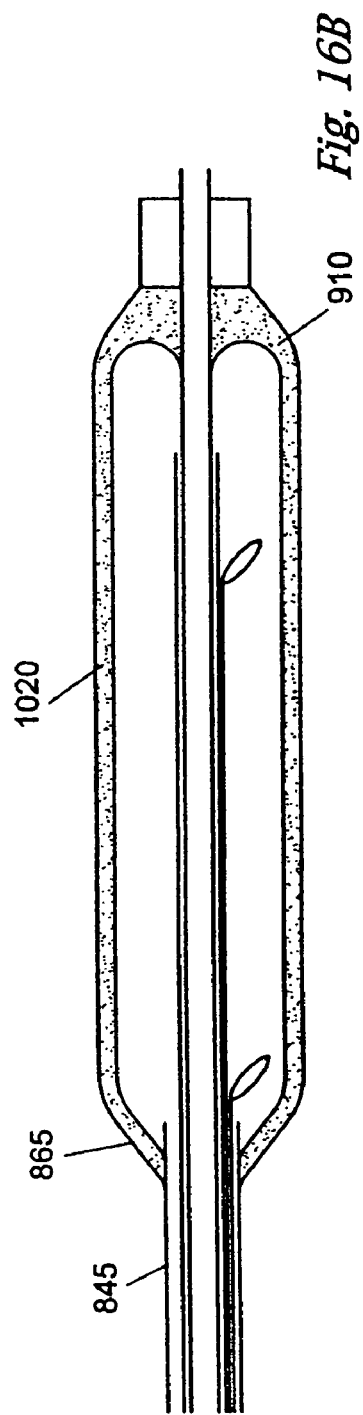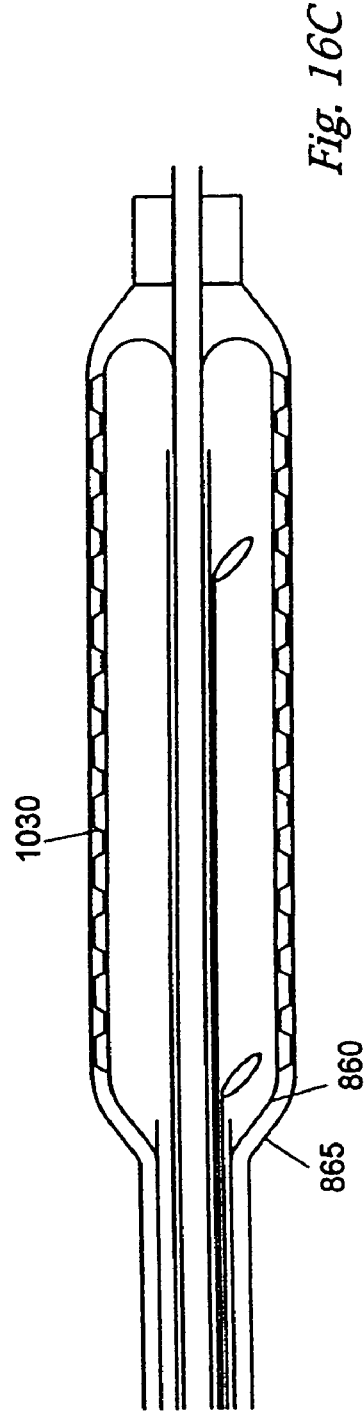

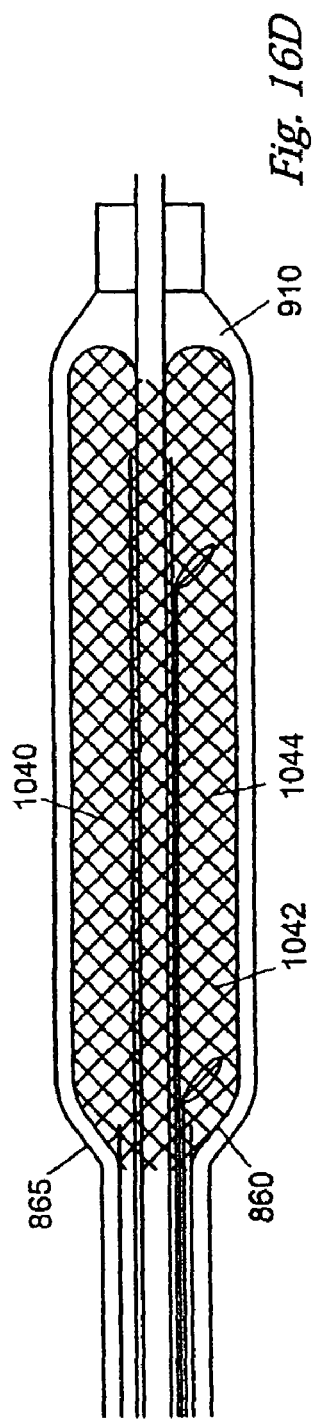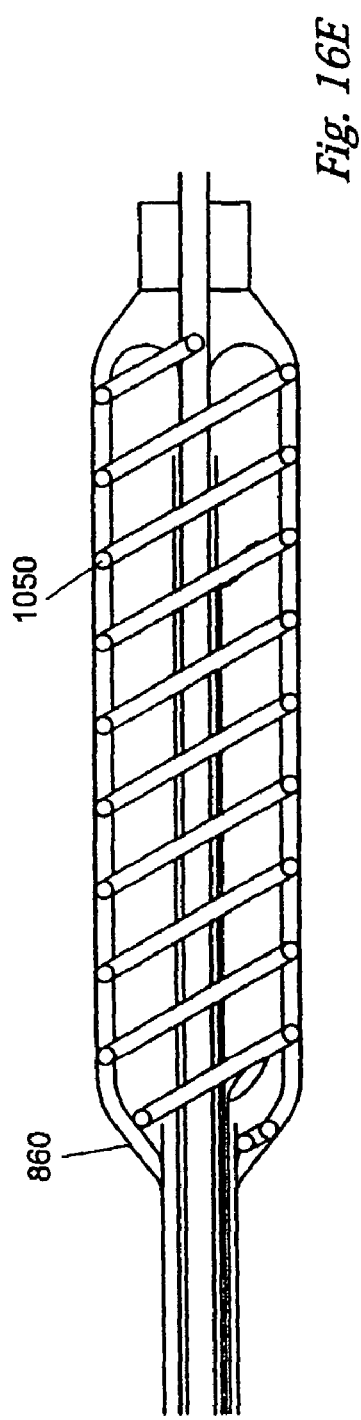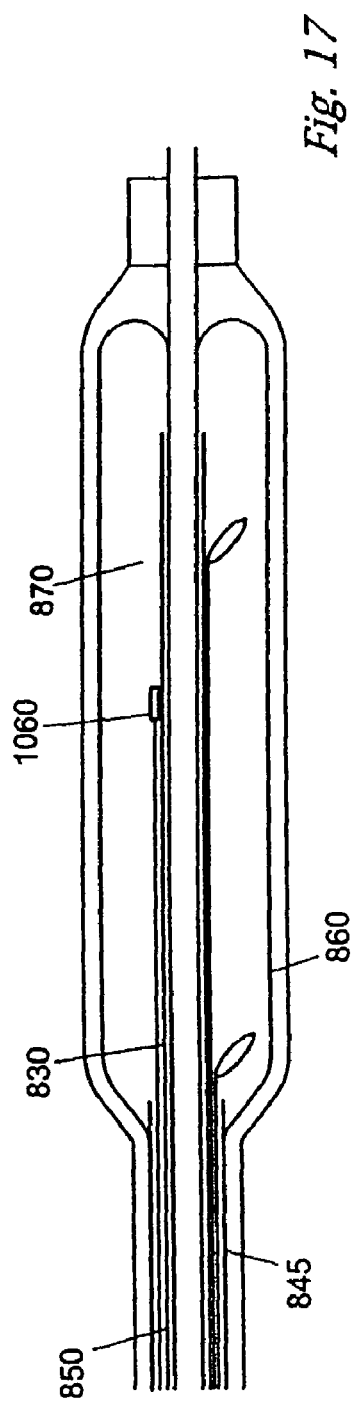

ENDOVASCULAR CRYOTREATMENT CATHETER

CROSS-REFERENCE TO RELATED APPLICATION

This application is a Divisional Application of application Ser. No. 10/397,619, filed Mar. 26, 2003, by Miriam Lane, et al., entitled ENDOVASCULAR CRYOTREATMENT CATHETER, now issued U.S. Pat. No. 7,300,433, which Application is a Continuation of and claims priority from application Ser. No. 09/945,319, filed Aug. 31, 2001, by Miriam Lane, et al, entitled ENDOVASCULAR CRYOTREATMENT CATHETER, now issued U.S. Pat. No. 6,575,966, which application is a Continuation-in-Part of and claims priority from Utility patent application Ser. No. 09/378,972, filed Aug. 23, 1999, by Jean Pierre Lalonde, entitled ENDOVASCULAR CRYOTREATMENT CATHETER, now issued U.S. Pat. No. 6,283,959, the entirety of all of which are incorporated herein by reference.

STATEMENT REGARDING FEDERALLY SPONSORED RESEARCH OR DEVELOPMENT n/a

FIELD OF THE INVENTION

The present invention relates to endovascular catheters, and in particular, to catheters for cry treatment of tissue.

BACKGROUND OF THE INVENTION

The present invention relates to endovascular cryocatheters, such as angioplasty balloons having a freezing function for treating tissue by extreme cooling contact. These catheters have an elongated body through which a cooling fluid circulates to a tip portion which is adapted to contact and cool tissue. Such a device may include a steering assembly such as an inextensible pull wire and a flexible tip to which the pull wire attaches which may be bent into a curved configuration to aid its navigation through blood vessels to a desired treatment site. When used for angioplasty or the destruction of tissue on the inner wall of a vessel, the catheter generally also has one or more inflatable balloon portions which may serve two functions of displacing blood from the treatment site to allow more effective cooling, and physically distending the affected vessel to break up accumulations of plaque.

Endovascular catheters must be of relatively small diameter, and configured for insertion along relatively confined pathways to reach an intended ablation site. As such, the cooling fluid must circulate through a relatively long and thin body yet apply significant cooling power in their distal tip. The requirement that coolant be localized in its activity poses constraints on a working device. For example, when the catheter must chill tissue to below freezing, the coolant itself must obtain a lower temperature to offset the conductive warming effects of adjacent regions of body tissue. Furthermore, the rate of cooling is limited by the ability to circulate a sufficient mass flow of coolant through the active contact region. Since it is a matter of some concern that proximal, adjacent or unintended tissue sites should not be exposed to harmful cryogenic conditions the flowing coolant must be exposed in a limited region. One approach to cooling uses a phase change refrigerant which is provided through the body of the catheter at relatively normal or ambient temperature and attains cooling only upon expansion within the tip region. One such device treats or achieves a relatively high rate of heat transfer by using a phase change coolant which is pumped as a high pressure liquid to the tip of the catheter and undergoes its phase change expanding to a gas in a small chamber located at the tip. The wall of the chamber contacts the adjacent tissue directly to effect conductive cooling or ablation treatment. Other cryocatheters may employ gas at high pressure, and achieve cooling via the Joule-Thomson effect at a spray nozzle in a cooling chamber at the distal end of the catheter.

In an endovascular catheter as described above, a relatively high cooling power may be obtained. However, the expansion of a phase change or high pressure coolant exiting from a nozzle within a small catheter tip creates highly turbulent flow conditions. The cooling region of the tip may be implemented as a fairly rigid chamber having highly thermally conductive wall or section of its wall formed for example by a metal shell. However, if one were to replace such a tip with an inflatable balloon as is commonly used for angioplasty, the size of the chamber would vary considerably as the balloon is inflated, causing substantial variations in flow conditions of the fluid entering the tip and substantial changes in heat transport across the expanding balloon wall. Both of these factors would result in variations of the cooling power over the tip. Furthermore, coolant materials suitable for high pressure or phase change refrigeration may pose risks when used within a blood vessel. Accordingly, there is a need for an improved catheter construction for cryogenic angioplasty.

Another factor which adds complexity to the task of cryocatheter design is that the primary mechanism of treatment involves thermal conduction between the catheter and a targeted region of tissue. Thus, not only is the absolute cooling capacity of the catheter important, but the nature and extent of contact between the cooled region of the catheter and the adjacent tissue is important. Effective contact may require moving, positioning, anchoring and other mechanisms for positioning, stabilizing and changing the conformation of the cooled portion of the catheter. Slight changes in orientation may greatly alter the cooling range or characteristics of the catheter, so that even when the changes are predictable or measurable, it may become necessary to provide positioning mechanisms of high stability or accuracy to assure adequate treatment at the designated sites. Furthermore, it is preferable that a vessel be occluded to prevent warming by blood flow during treatment. Beyond that, one must assure that the cooling activity is effective at the surface of the catheter, and further that defects do not cause toxic release of coolant or dangerous release of pressure into the body.

Secondary environmental factors, such as the circulation of blood near or at the treatment site may also exert a large influence on the rate at which therapeutic cooling accrues in the targeted tissue.

There is therefore a need for improved catheter constructions to occlude blood flow and form a dependable thermal contact with a vessel wall.

Additionally, the operation of such a device for therapeutic purposes requires that the coolant be contained within the catheter at all times, lest a leak of coolant enter the body and thereby cause significant harm. Known catheters which employ inflatable balloons often inflate the balloons to relatively high pressures, that exceed the ambient pressure in a blood vessel or body lumen. However, to contain the coolant, these catheters generally employ thicker balloons, mechanically rigid cooling chambers, and other similar unitary construction containment mechanisms. These techniques however, lack robustness, in that if the unitary balloon, cooling chamber, or other form of containment develops a crack, leak, rupture, or other critical structural integrity failure, coolant may quickly flow out of the catheter.

There is therefore, for security purposes, a need for improved cryocatheter constructions to robustly contain coolant flow when cryotreatment is performed.

Finally, a major challenge for effective cryotreatment is the ability to fine tune the pressure and temperature of the coolant flow at the distal tip of the catheter, so as to controllably apply cooling to adjacent tissue. The cooling power of the device, created through the Joule-Thomson effect and phase change of the coolant as described above, is generally inversely proportional to the resultant coolant pressure achieved after injection into, and during flow through, the cooling chamber or balloon. Thus, in order to maintain the balloon pressure at safe levels, without exceeding ambient body pressures, the device must be operated at relatively lower balloon pressures, which have the undesired effect of raising the cooling power to levels which are difficult to control and may even harm or damage the target tissue. Therefore, the enhanced cooling power of the device achieved under such relatively low operating pressures must be mitigated by providing some form of tunable thermal resistance between the coolant flow and the target tissue.

It is desirable therefore, to provide for an improved catheter system which may safely operate at low balloon pressures while thermally insulating the target tissue from excessive cooling.

SUMMARY OF THE INVENTION

In a first embodiment of the present invention, a body insertable cryotreatment catheter is configured with an elongate catheter body, and distal cooling tip assembly having a cooling chamber surrounded by an expandable member. The expandable member surrounds the cooling chamber to define an interstitial space therebetween. The interstitial space is in fluid communication with a vacuum source. The cooling chamber may be rigid or flexible. A coolant injection lumen is provided in the catheter body such that the cooling chamber is inflatable by the flow of coolant from the injection lumen. Primary and secondary return lumens are in fluid communication with the cooling chamber and interstitial space, respectively, to: (i) define first and second pathways for the flow of coolant, respectively, (ii) contain the coolant flow within the catheter body in the event of structural failure of the cooling chamber, and (iii) to provide supplemental thermal insulation around the cooling chamber. At least one of the inner surface of the expandable member or the outer surface of the cooling chamber may be modified to be topographically non-uniform, so as to provide for a larger interstitial space volume than in the absence of such modification.

In another embodiment of the present invention, a catheter comprises a handle in fluid communication with a supply of cooling fluid having a boiling temperature, a source of vacuum, a cooling chamber having fluid impermeable inner and outer surfaces, and an elongate catheter body having a coolant injection lumen having proximal and distal end portions, the proximal end portion being in fluid communication with the supply of cooling fluid, the distal end portion being in fluid communication with the cooling chamber. The catheter further comprises a primary return lumen having proximal and distal end portions, the proximal end portion being in fluid communication with the source of vacuum, the distal end portion being in fluid communication with the cooling chamber. The catheter also includes an expandable member having inner and outer surfaces coupled around said cooling chamber, wherein a space exists between the cooling chamber outer surface and the expandable member inner surface. Furthermore, a secondary return lumen is disposed within the catheter body, having proximal and distal end portions, the proximal end portion being in fluid communication with the source of vacuum, the distal end portion being in fluid communication with the space.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 illustrates a balloon catheter system in accordance with a first embodiment of one aspect of the present invention;

FIG. 2 shows a cross section taken along the axial direction through the balloon portion of another embodiment of the invention;

FIG. 4 illustrates another embodiment of the invention;

FIG. 5 illustrates balloon orientation;

FIG. 7 illustrates another two balloon cryocatheter;

FIG. 7A illustrates a section through a multilumen catheter suitable for the practice of the invention;

FIG. 13 shows a cross section taken along the axial direction of a dual balloon catheter system;

FIG. 13A illustrates a transverse cross-section of the catheter body along lines A-A in FIG. 13;

FIG. 14 illustrates a cross section taken along the axial direction through the distal portion of the catheter system of FIG. 13;

FIG. 15 illustrates the catheter system of FIG. 14, when the outer balloon is under vacuum pressure;

FIGS. 16A, 16B, 16C, 16D, and 16E illustrate various alternative embodiments of the catheter system of FIG. 14; and FIG. 17 shows the catheter system of FIG. 14 with a pressure transducer located in the inner balloon.

DETAILED DESCRIPTION OF THE INVENTION

Figure 3A:
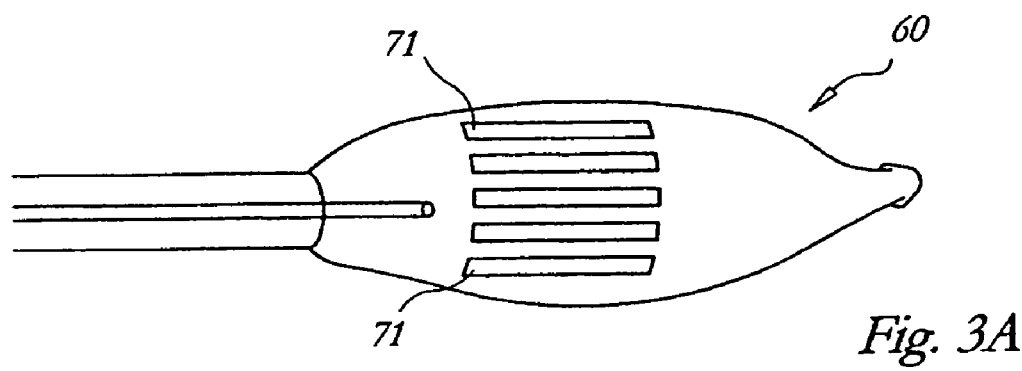
FIGS. 3A-3D illustrate four embodiments of thermally conductive balloons in accordance with the invention.

FIG. 1 illustrates a treatment catheter 10 in accordance with a basic embodiment of the present invention. Catheter 10 includes a handle 10a, an elongated intermediate body portion 10b, and a distal end 10c. An inextensible guide wire 21 extends from the handle to the tip 10c for exerting tension via a take up wheel 22 that is turned by lever 24 to curve the tip of the catheter and steer it through various branch points along the route through a vessel to the intended treatment site. Alternatively, the catheter may be provided with a central guide wire lumen. In that case, a guide wire is inserted into the vessel up to or past the treatment site and the catheter is then placed over the guide wire. As further shown in FIG. 1, a balloon 30 is attached to the distal end of the catheter and as described further below is in communication via the intermediate body 10b and handle 10a with an inlet 40a for the refrigerant fluid, and an outlet 40b through which spent refrigerant returns. The handle may also receive electrical connections via a port or cable 45 for various sensing or control functions described further below.

General principles concerning the construction or operation of such a cryocatheter may be found in U.S. Pat. No. 5,281,215 which is incorporated herein by reference for purposes of disclosure and illustration.

In accordance with one aspect of the present invention, the refrigerant fluid applied at the port 40a is applied through a first passage to the balloon and returned from the balloon through a second passage to the outlet 40b, at a positive pressure. For example, a valve may be present downstream of the balloon to set a back pressure which effects inflation of the balloon by the coolant fluid. As illustrated in FIG. 1, the valve may be implemented by a check valve 51 positioned at the port 40b and set for example to open at a pressure of 10 psig to maintain a sufficient back pressure in the return line for inflation of the balloon 30. In alternative embodiments, the check valve 51 may be replaced by a controllable valve, or a pressure sensing arrangement that provides a feedback signal in conjunction with an electrically controlled valve, to assure that the desired inflation pressure is achieved at the balloon 30 while allowing return of coolant continuously through the outlet 40b to a control console. In either case, the return valve maintains a minimum pressure at the outlet side of the catheter assembly. This minimum pressure is at a level higher than blood pressure to assure that the balloon inflates and occludes the vessel in which it is located.

In one embodiment, a relatively thin balloon is placed at the end of the catheter and is folded over the shaft so that when the coolant fluid is injected, the balloon opens and inflates to occlude blood flow within the vessel where it is situated. By increasing the injection pressure to the balloon, the rate of cooling is increased to apply cryogenic conditions at the surrounding wall of the vessel. Preferably, a refrigerant such as liquid $CO_2$ is employed having relatively controllable thermal characteristics for the desired treatment range. Leakage of $CO_2$ into the blood stream, if it occurs, is harmless in small amounts. This construction may be varied somewhat. For example, the balloon may be a relatively thick-walled balloon intended when inflated to exert mechanical force against the vessel wall to break up plaque. In that case, relatively higher inflation pressures are used, and the outlet valve 51 may be operated to maintain back pressures up to several atmospheres or more. Furthermore, it will be understood that the relatively small cross-sectioned opening present in the body 10d of the catheter may itself operate to cause a pressure drop, or back pressure, so that the valve 51 may be set to a lower opening pressure threshold, so long as back pressure at the balloon is maintained sufficiently high in the range for balloon inflation.

In accordance with one aspect of the present invention, the balloon operates to treat adjacent vascular tissue by freezing.

This is achieved in one preferred aspect of the invention by a balloon fabricated with a wall metallization that enhances the heat transfer rate through all or a portion or pattern of the balloon wall. FIG. 2 is a cross-sectional view through one such balloon 60 taken in a plane along the axis of the device. As shown, the balloon 60 is attached to the end of the catheter shaft 10b and has a refrigerant injection tube 4 extending to its interior so that refrigerant flows out the end or other apertures which are provided in the distal portion of the tube 4 and fills a chamber 62 defined by the interior of the balloon. A guide wire lumen 6 may extend to the distal tip for facilitating insertion, and a steering wire (not shown) may be positioned in the adjacent portion of the tip or extend through the balloon, in a manner generally known in the art of catheter design to deflect the tip portion. Within the body of the catheter shaft 10b, the region of the lumen not occupied by the injection tube and other described components serves as a return passage for the refrigerant released from the nozzle end 1 of the injection tube 4. As further shown in FIG. 2, the balloon 60 has a wall of membrane thickness with a pattern of metallization, visible as metal regions $64_a$, $64_b$ ... $64_c$ disposed over its surface. The patterned metallization regions 64 have higher thermal conductivity than the bulk balloon membrane material, and define regions at which destructive freezing contact to the vessel wall itself will occur when the balloon is inflated.

FIGS. 3A through 3D illustrate various patterns suitable for use in the present invention in perspective view on a representative balloon 60. As shown in FIG. 3A, one such pattern includes a plurality of substantially axially oriented lines 71 disposed around the circumference of the balloon. The balloon is shown in a partially inflated posture. When inflated more fully, the balloon expands and the lines 71 move apart around the circumference. Since expansion occurs only in the radial direction, the metal does not constrain expansion of the balloon or introduce localized stresses or cracking during expansion.

Figure 3B:
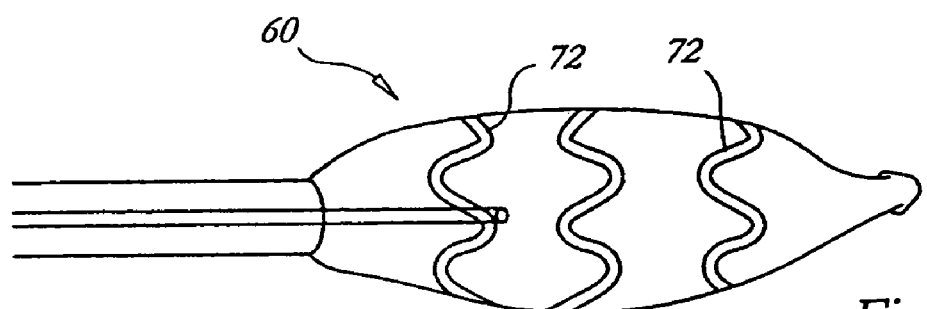

FIG. 3B shows a second useful pattern in which the conductive pattern include a zigzag or meandering arrangement of conductive metal portions 72 configured such that bends or junctions of successive path region allow the balloon to expand without constraint. In this case, radial enlargement and circumferential expansion of the balloon wall simply bends the metal paths. In general, any of the shapes which have been found suitable for expanding metal mesh, wire or coil stents may be useful as surface patterns for the balloon membrane to enable it to undergo radial expansion without introducing mechanical faults into the balloon membrane.

Figure 3C:
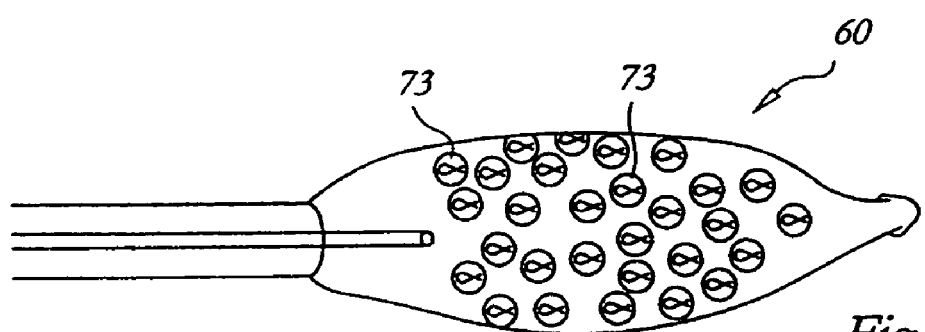

The invention also contemplates conductive patterns in which the conductive regions consist of a plurality of substantially separated or disjoint small loci. These may consist of solid regions such as dots 73, or squares or rectangles of relatively small overall extent, e.g., under several millimeters across, to produce dimpled regions of conduction extending over the whole surface of the balloon as shown in FIG. 3C, or may include one or more large areas so as to adapt the balloon for applying a particular pattern of localized cooling, such as a cooling through on side of the balloon while still allowing the balloon to expand in its entirety to firmly lodge the balloon within the vessel and displace blood so as to allow the cooling surface of the balloon to effectively and directly contact the vessel wall.

Figure 3D:
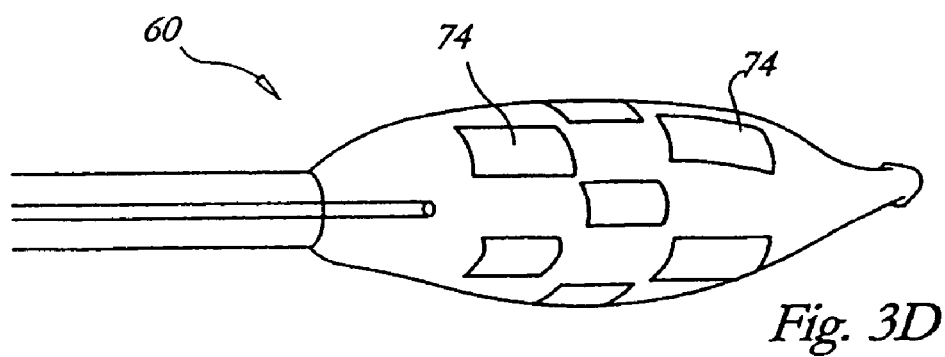

FIG. 3D shows another useful pattern 74 for the balloon.

The metal or conductive regions 71, 72, 73 and 74 may be applied using lithographic printing technology, for example, by applying a metal-loaded thermally conductive ink in a polymer base to the membrane, or by applying complete coatings and patterning and etching away regions by lithography techniques to form the desired pattern. Such patterns may also be formed by applying a metal foil layer or depositing such a layer by plating or sputter deposition techniques and employing lithographic methods to pattern the continuous layers. In general the pattern is formed so as to create a desired pattern of icing lines for effectively destroying tissue at the patterned areas of conductive contact when the balloon is inflated. The conductive regions 64, 71-74 may also be created by adding thermally conductive materials such as copper powder, flakes or fibers to the material of the balloon membrane itself. In that case the powders or fibers are preferably mixed with the appropriate elastomer or polymer material from which the balloon is to be formed, and the balloon is then formed by a known technique such as molding, forming on a mandrel, dipping or other common balloon forming technique. When patterning is desired, a standard elastomer and a conductively loaded elastomer may be painted on in bands or otherwise patterned during the manufacturing process to create the desired thermal contact regions.

FIG. 4 illustrates another embodiment 80 of the present invention. This embodiment has a multi-balloon structure and a cooling segment 84 at the catheter tip. As illustrated, segment 84 corresponds to the expansion chamber or region of greatest cooling activity of the catheter and includes a cooling pattern assembly. This may be a spiral metal wrapping that provides stiffness, form and thermal conductivity to the segment. A first balloon 82 is positioned on one side of the cooling segment 84 to serve as an anchor and blood vessel occluder or flow blocker, and in this embodiment a second balloon 86 extends from the other end of the cooling segment. As shown, the first balloon is substantially ovaloid and symmetrical, while the second balloon 86 has a tapered, trumpet- or bell-shaped aspect that allows it to wedge at the end of a vessel, for example, in the ostium or junction of the vessel end to an organ. Thus, while the balloon 82 is inflatable within a vessel to serve as an anchor, balloon 86 is adaptable to fit in an opening and occlude the opening, or define an end-contact geometry for positioning the cooling segment 84 in close proximity to the vessel end opening.

It will be appreciated that the cooling segment 84 in this embodiment has a relatively fixed diameter and is not subject to inflation. Rather it has high thermal conductivity and in use when actuated by flow of refrigerant within the catheter, an ice ball forms to extend its thermal range. The region of ice formation is indicated schematically by the external dotted profile positioned around the cooling segment of the catheter.

As further shown in FIG. 4, the catheter assembly may include a guide wire lumen 87 for over-the-wire insertion, or for monorail guiding movement of the distal tip. Alternatively, the distal termination may include a conventional wiggler tip or a steering assembly manipulated from the handle end of the catheter. Furthermore, the positions of the balloons 82 and 86 may be interchanged, with the anchor balloon 82 being positioned distal to the cooling segment 84 and the tapered or trumpet balloon 86 positioned proximally thereof. This configuration allows use of the catheter by insertion along the opposite direction of the vessel, for example, through a cardiac chamber and into a vessel exiting the chamber.

Thus, in accordance with this aspect of the invention, the cryocatheter includes a cooling segment that is positioned and anchored by one or more occlusion balloons. Preferably at least one of these balloons is inflated with the carbon dioxide or other biocompatible refrigerant from the cooling segment. The balloons are not necessarily of equivalent dimension, geometry or compliance. The anchoring balloon may be inflated via an individual inflation lumen, thus allowing the position to be precisely set and this balloon inflated before cooling is initiated. The tapered balloon may be inflated in multiple ways depending on the desired effect. For example, when it is desired to treat a lesion in a vessel in close proximity to the ostium, for example, in the renal arteries, the catheter may be configured such that the coolant both inflates and cools the balloon 86, so that its tapered surface is a contact cooling surface for treating the adjacent vessel tissue.

In another embodiment, an individual inflation lumen may be provided for the flared balloon 86. In that case, this balloon may be inflated first when it is desired, for example, to place the cooling segment 84 in close proximity to the ostium. Balloon 86 may then serve the function both of positioning the cooling segment, and of occluding blood flow in the treated region. Thus, the catheter of FIG. 4 may be used for cryogenic treatment in a blood vessel and is well adapted to forming lesions near or at the ostium of the vessel. As noted above, by reversing the positions of balloons 82 and 86, the catheter may be navigated from the opposite direction along a vessel to treat a site near a junction. Furthermore, by reversing the taper orientation of the balloon 86, the catheter may be configured to more effectively treat a junction of particular size and accessible from one orientation.

In yet another embodiment, the catheter is manufactured without the symmetric anchoring balloon 82 and carries only the cooling segment 84 and trumpet balloon 86 at its tip, forming a configuration for making relatively linear lesions in locations where the vessel diameter changes rapidly. For example, such a modified catheter may be used for treatment in an antegrade approach to a treatment site along the femoral artery, as shown in FIG. 5.

Figure 6:
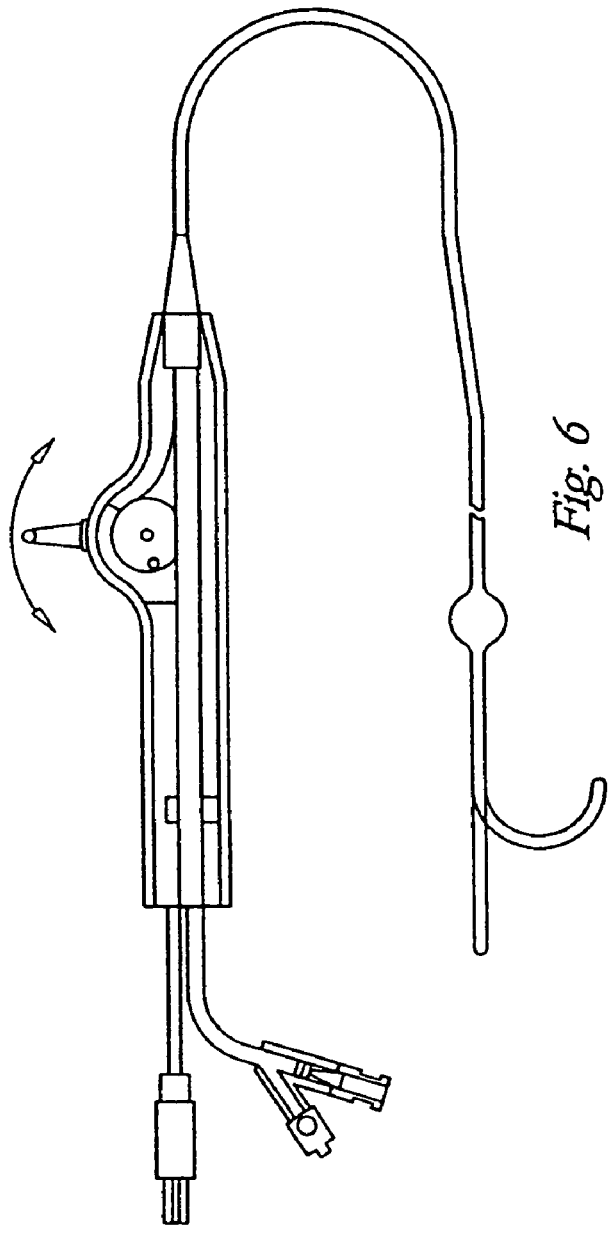
FIG. 6 illustrates an embodiment with proximal anchoring/occlusion balloon.

FIG. 6 shows another embodiment of the invention. This embodiment is similar to that of FIG. 1, but the catheter tip is configured so that rather than applying cryogenic cooling through an expandable balloon, the cooling segment is of substantially fixed diameter, which may be comparable to that of the catheter body, and it extends distally from a proximal balloon which functions to occlude the blood vessel in which the catheter lies. As shown, the tip portion is deflectable by means of a tension wire connected to the handle, so as to more effectively navigate along vascular branching passages. The tension wire may also be operated to urge the cooling segment into contact at the intended target site. As in the embodiment of FIG. 1, the coolant is preferably liquid carbon dioxide, and the coolant return line is kept at a pressure higher than the nominal blood pressure in the vessel being treated. The balloon may thus communicate with the return flow of gas so that the returning coolant inflates the balloon and effectively occludes the vessel. By placing the balloon sufficiently far downstream from the cooling segment or liquid expansion opening, the return gas may be warmed sufficiently to avoid freezing tissue in the balloon occlusion region. Similarly, by locating the balloon closer to the freezing segment, the cooler carbon dioxide will provide cryogenic treatment through the balloon surface to an additional region of tissue adjacent the cooling segment. In further embodiments, a distal balloon (not shown) may also be provided. A limiting orifice is preferably placed in the catheter lumen between the coolant injection tube and the distal balloon to prevent cold gas from entering the balloon too rapidly. Thus, the distal balloon is trickle-filled from the expansion region of the catheter to provide dependable occlusion or anchoring without damaging surrounding tissue.

In any of the foregoing embodiments, applicant contemplates that a valve release, or an actively-switched vacuum connection may be provided to quickly deflate the balloons on demand by reducing back pressure of the return lumen in the catheter body.

FIG. 7 shows another embodiment 90 of the invention, illustrated by way of an axial cross-section taken in a diametral plane through the tip of the catheter. As shown, the tip of the catheter includes a pair of balloons 92a, 92b surrounding a cooling segment 93. As shown, the cooling segment and balloons may be formed by a common cylindrical membrane surrounding the catheter body, while the elongated catheter body provides necessary lead in and return passages for inflation of the balloons and delivery of cooling fluid. The cooling segment possesses a heat exchanging surface 93a which may also be a metallic or structural component of the device. For example, the surface indicated by elements 93a in the Figure may be formed by a metal spring surrounding the body, or by a metal coating or foil lithographically etched to form a coil embedded in or surrounding the membrane. Alternatively, or in addition, the cooling segment may be implemented by a helically slotted coolant supply tube fixed in the lumen of the catheter shaft to preferentially direct the coolant in liquid form against the wall of the coolant segment. In this embodiment, the catheter shaft 91 is preferably a multilumen shaft, implemented as shown, for example, in FIG. 7A. The lumena may include, in addition to a guide wire lumen if one is provided, a lumen 94 for coolant delivery, a larger return lumen 94c which may surround the delivery lumen, and one or more auxiliary lumens 94a, 94b. In various embodiments the auxiliary lumens are connected via the handle to separately inflate one or more of the balloons 92a, 92b. Alternatively, when balloon inflation is performed by trickle inflation of gas from the cooling segment 93, an auxiliary lumen may be used for a controllable vacuum passage which is actuated to deflate a balloon. As noted above, inflation of the balloons may be effected by the spent or warmed phase change coolant gas in its course towards the return lumen.

When balloon inflation is entirely effected by gas from the cooling segment, one or more of the lumena may be used to contain a steering wire or other accessory unrelated to fluid transfer. Thus as illustrated in FIG. 7, the catheter 90 may be configured with a guide wire lumen 95 for navigation within a vessel, or may include a steering and support wire assembly 98 within the catheter body to aid insertion. The invention also contemplates that, in a manner similar to the embodiments described above, the catheter 90 may be implemented with a single occlusion balloon, which is preferably placed proximal to the cooling segment for antegrade approaches to lesion treatment. Alternatively, the balloon may be placed distally of the cooling segment when it is desired use the device for treating lesions by a retrograde approach. When both occlusion balloons 92a, 92b are present, the cooling segment is readily anchored in short, branched or turning passages by inflating one or both balloons. The balloons may further be of different sizes or may be shaped as discussed above for particular applications and vessels.

Figure 8A:
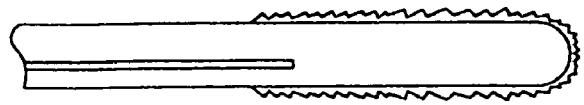
FIGS. 8A and 8B show another balloon embodiment of the invention in its deflated and inflated state, respectively.
Figure 8B:
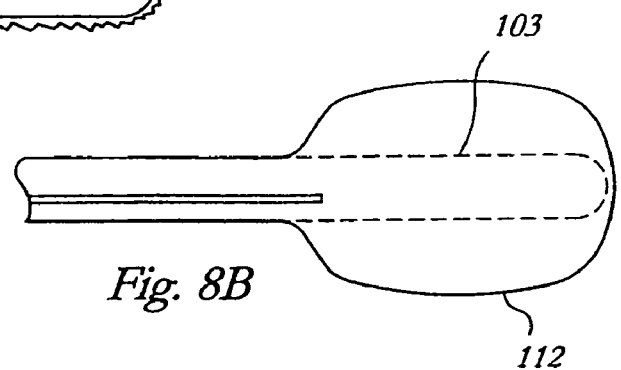

In addition to the specific embodiments discussed above, in one aspect of the present invention, the invention include a balloon disposed as an annular chamber or cuff around a cooling assembly. Such an embodiment is shown in FIGS. 8A and 8B. In accordance with this aspect of the invention, the catheter 10 carries a coolant injection tube 1 which extends to a cooling chamber structure 103 that is surrounded by a cooling balloon 112. The cooling chamber structure 103 is relatively stiff or even rigid and has substantially fixed dimensions. It may be implemented, for example with a cylinder formed of hard polymer or metal and having a fixed diameter. Surrounding the cooling chamber cylinder 103 is a balloon 112 shown in its deflated state in FIG. 8A and shown fully inflated in FIG. 8B. When the cooling and balloon inflation are carried out by the same medium, the cooling chamber 103 may be implemented with a perforated chamber wall. The use of a substantially rigid chamber 103 allows the coolant flow upon exiting the injection tube to undergo substantially regular conditions and therefore provides well regulated and predictable cooling characteristics. However, the invention also contemplates that the balloon may be inflated with a pressurizing medium other than that provided by the refrigerant. In either case the balloon may be formed of a quite thin membrane, on the order of 0.02 millimeters thickness or less, so that in this case it presents very little impediment to heat conduction.

In this construction, the balloon serves as a compliance member to conform to irregular tissue surfaces, and may be used to apply pressure to a lumen to enlarge the lumen in a manner similar to that employed in coronary angioplasty and fallopian tuboplasty procedures. The balloon may also be operated to occlude blood flow when used in an endovascular catheter for rapid therapy since the inflation portion may be deployed or deflated substantially instantaneously. The balloon further operates to center the cooling chamber within the lumen, thus assuring substantially concentric cooling characteristics for the treatment. Finally, the balloon serves to anchor the cooling chamber in position.

The provision of a fixed dimension cooling chamber surrounded by an annular balloon that is inflated by a separate medium, advantageously provides an enhanced spectrum of operating characteristics. Several examples follow illustrating the range of this construction of the invention.

Figure 9A:
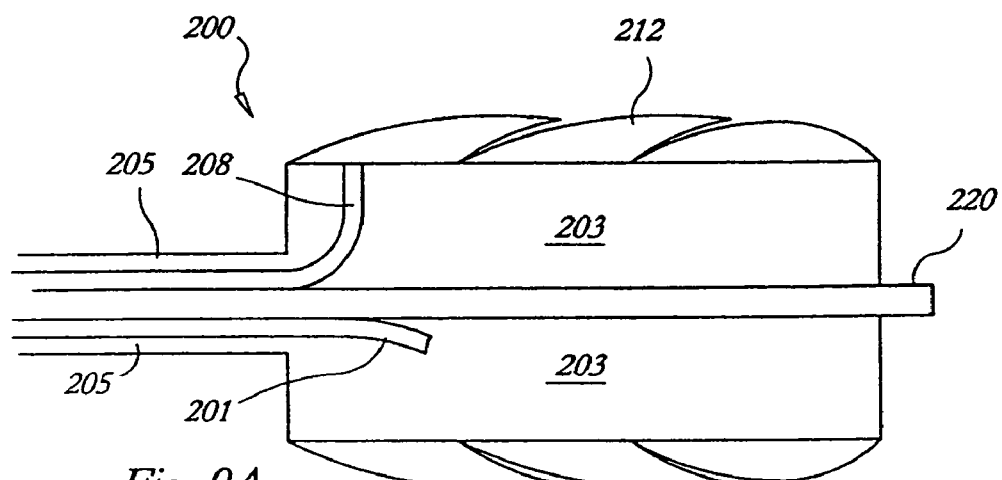
FIGS. 9A and 9B show a balloon embodiment with separate cooling and inflation media.
Figure 9B:
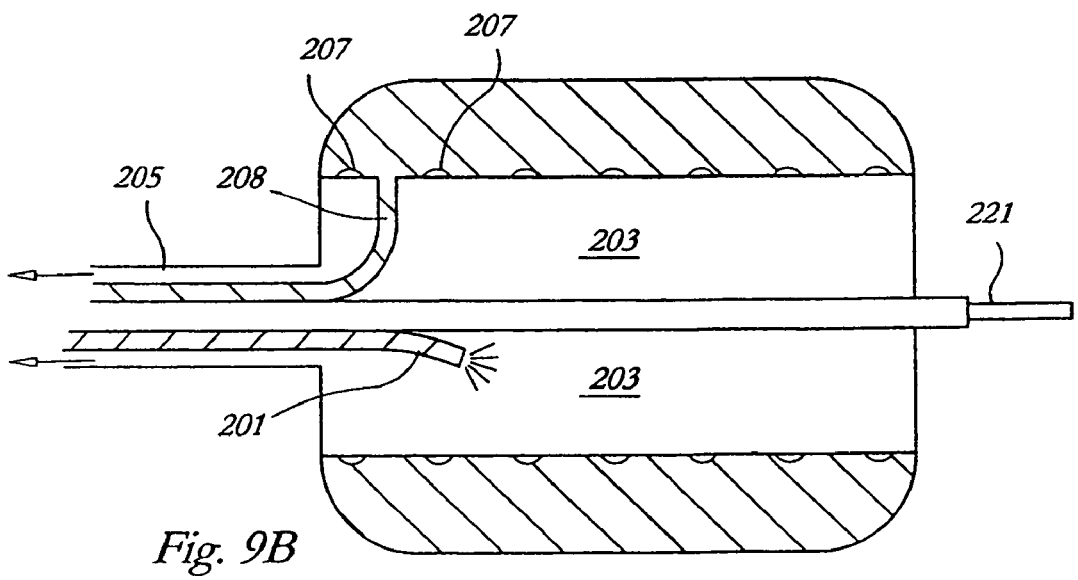

FIGS. 9A and 9B schematically illustrate the construction of a guide wire cryocatheter 200 having such a circumferential cushioning balloon 212. This construction may also be applied to cooling other cylindrical tissue structures or body lumens, including organs or structures such as the fallopian tube, esophagus, biliary duct, ureter, gastrointestinal tract and the bronchus. For each of these different applications, the relative diameter of the cooling chamber and the thickness of balloon portion may be varied so as to achieve for example high total cooling with a large cooling chamber and an effective rate of heat transfer from the surrounding tissue area through a relatively thinner layer of cooling balloon. Notably, the balloon may inflated with a medium such as precooled saline solution having a high rate of thermal conductivity and a high thermal storage capacity, to achieve quick chilling and to maintain a stable thermal set point without having to design the cooling chamber to bear the full thermal load alone.

As shown in FIG. 9A, the injection tube 201 enters the expansion chamber 203 and injects refrigerant at high pressure, which then expands in the chamber and is exhausted through the exhaust lumen 205 which constitutes the major portion of the catheter shaft. The balloon 212, shown in its collapsed state in FIG. 9A around the circumference of the cooling chamber, is inflated via a balloon inflation lumen 208. Applicant contemplates that the balloon inflation may be effected by a number of inflation media, including a gaseous coolant medium from the other (coolant) chamber 203. However, preferably, in this embodiment an incompressible liquid such as saline solution having a high thermal capacity and excellent heat conductive properties is applied through the inflation tube 208 to fill the balloon as shown in FIG. 9B. The external surface of the expansion chamber 203 may be provided with texture, such as a plurality of isolated bumps or dimples 207, of which several are shown in cross-section, to provide unobstructed fluid percolation passages along the surface and assure that the balloon inflation fluid may have free access and flow quickly to and from the passage 208. This allows the balloon to fully deflate when fluid is withdrawn via passage 208.

A guide wire lumen 220 passes centrally through the cooling chamber assembly and as shown in FIG. 9B accommodates a guide wire 221 for directing and positioning the catheter. As further shown in those Figures, the outer diameter of the cooling chamber may extend for a relatively great portion of the total diameter of the device so that the balloon portion occupies only a thin shell which effectively extends the reach of the cooling chamber and provides a short heat conduction path together with firm compliant contact with surrounding tissue. As noted above, when used for angioplasty and other cryogenic treatment contexts the balloon serves to apply a stretching or extensile force to tissue, which is conducive to the desired tissue treatment destruction or regeneration process. The provision of such enlarged cooling chamber also provides a greater external surface area for the coldest central structure of the catheter, greatly enhancing the rate of thermal transfer achieved with the balloon assembly.

In general the body of the catheter may be comparable to that of existing treatment devices, e.g., one to four centimeters in length for an endovascular angioplasty device. However the cryogenic portion need not extend the full length of the tip assembly, and the structure may include axial extension portions which are not cryogenically cooled.

Figure 10A:
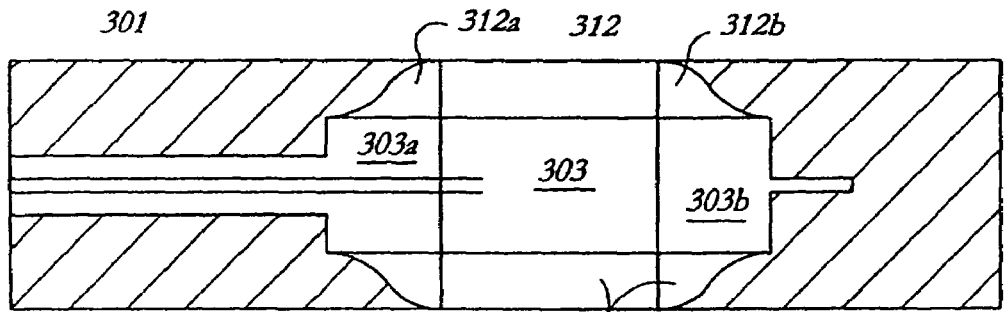
FIGS. 10A-10B show yet another balloon embodiment.
Figure 10B:
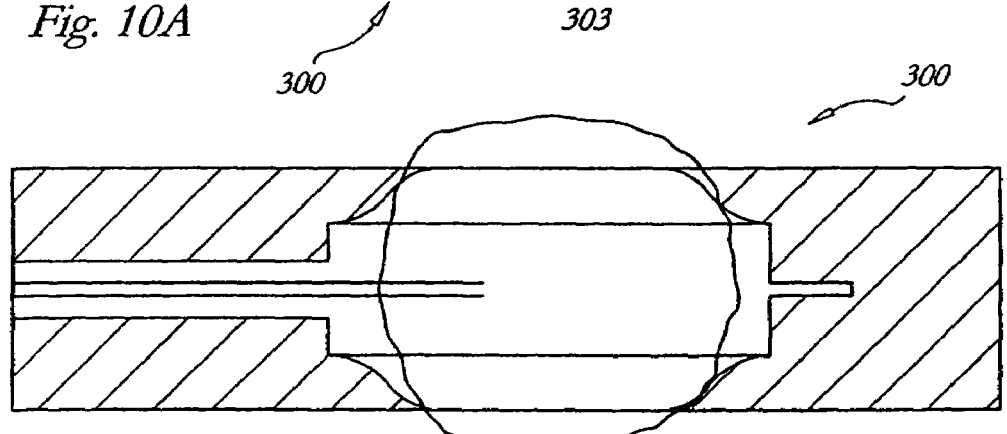
Figure 10C:
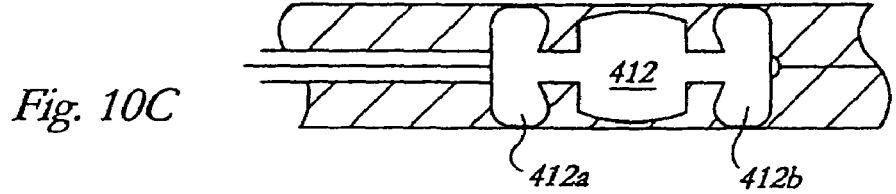
FIG. 10C illustrates a further variation on the embodiment of FIGS. 10A-10B.

FIGS. 10A through 10C illustrate a construction of a cryo-catheter 300 of this type. In this embodiment, the tip of the catheter includes chambers 303, 303a and 303b all located within the balloon. The chamber 303 serves as a cooling expansion chamber in the manner described above, and the cooling injection tube 301 opens into that chamber. At the proximal and distal ends of chamber 303, pair of dummy chambers 303a, 303b extend continuously with the main body of the chamber to form a single elongated cylindrical structure lying within the balloon 312. However, the end chambers 303a, 303b are isolated from the injected coolant, and themselves form dummy spaces or uncooled regions that serve simply to provide positioning support. As further shown in FIG. 10A, the balloon 312 has corresponding segments denoted 312a, 312b and 312c that are partitioned from each other such that the end segments are separated from the central cooling portion of the balloon. These segments lie over subchambers 303a, 303 and 303b. They may be serially connected or separately supplied with inflation material, so fluid entering the balloons is cooled only in the central region.

The illustrated embodiment of FIG. 10A has a generally continuous balloon contour in which at least a portion of the end segments 312a, 312b inflates to the diameter of the surrounding blood vessel or tissue lumen and serves to displace blood, fluid or tissue away from the cryogenic treatment portion at the center of the catheter tip. As shown in FIG. 10B, this has the effect of creating a cooling region that forms a relatively symmetrical ice ball volume (indicated by dashed lines in the Figure) around the vessel and catheter tip, with greater depth of penetration centered directly over the cryogenic chamber and with cooling damage tapering off away from that region. The balloon need not be a single continuous or partitioned balloon but may be implemented with separate balloons that in turn may be inflated via separate filler or inflation tubes (not illustrated) so as to more effectively achieve or more independently initiate the blocking and heat isolation functions. FIG. 10C illustrates one such embodiment 400, in which a cryogenic balloon 412 is surrounded by first and second blocking or blood displacing balloons 412a, 412b that are offset a short distance away from the ends of the coolant chamber. With this construction the excluding balloons may be positioned more remotely from the cryogenic segment.

In any of the foregoing embodiments, the balloon may be configured to apply a chilling level of cold without freezing or destroying tissue when appropriate for the tissue involved. As with the basic embodiment shown in FIGS. 8A and 8B, the catheter of the present invention preferably allows the withdrawal of sufficient thermal energy form the target site to freeze tissue, while the balloon anchors or enhances the positioning of the cryogenic source within the lumen so as to deploy the resulting ice ball in an appropriate relation to the surrounding tissue. The balloon enhances control of adjacent blood flow and may be used to arrest blood flow in the vessel entirely so that therapeutic cold accrues more quickly and is not dissipated. By actively pumping out the inflation fluid, collapse of the balloon following therapy allows more immediate resumption of circulation to perfuse tissue. Furthermore, by using a liquid-inflated balloon, the device may be deployed in much the same manner as an existing angioplasty catheter, and the guide wire lumen allows simple navigation and use of the device without requiring that the physician or cardiology specialist acquire additional operating skills or specialized training.

The catheter shaft may accommodate various lumens either as part of the shaft extrusion, or by carrying them as separate tubes such as an injection tube, a coolant exhaust lumen, a balloon inflation lumen, a guide wire lumen and other lumens, for example, for carrying wires to heating elements and/or monitoring devices to sense pressure, temperature and other sensing functions. By making the diameter of the cryogenic chamber large in relation to the targeted tissue lumen, the balloon may be formed with a low interior volume, facilitating the thawing of the inflation medium and reducing the time of total vascular obstruction. The thawing may further be advanced by providing and activating one or more heating elements, which may include any of a wide variety of heating means within the catheter body, such as resistive heating, radio frequency heating, laser heating applied via an optical fiber extending through the catheter body, microwave heating or heated gas or liquid infusion applied to the balloon portion. These may also include, in various treatment regimens, sources of energy that are externally applied to a catheter designed to preferentially receive such energy. Such external heating energy sources may, for example, be ultrasound or electromagnetic radiation applicators. The heater may also include various semiconductor, thin layer resistive or other similar technologies deployed, for example, on the balloon surface so as to heat one or more of the wall of the body lumen, the balloon inflation medium, or various pieces of the catheter structure.

Figure 11:
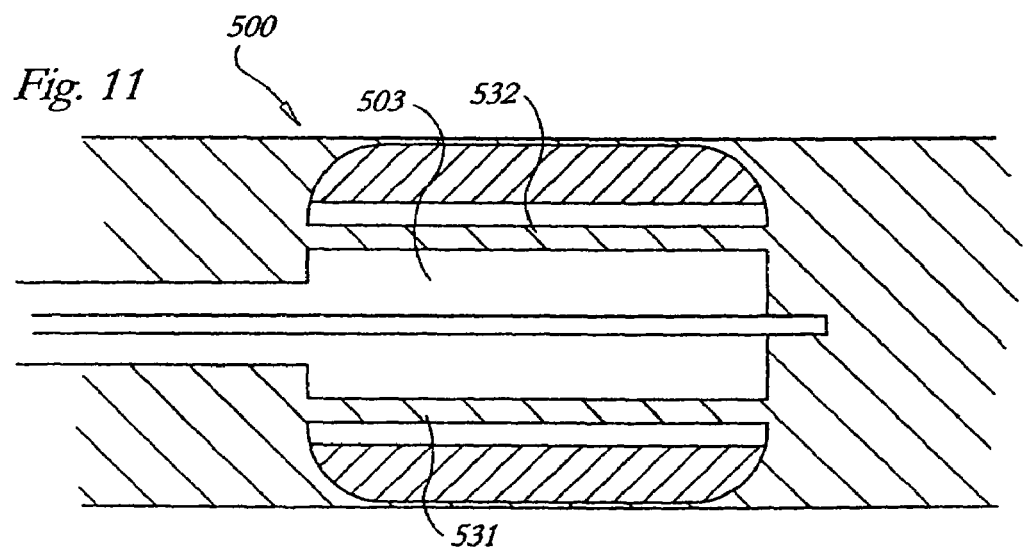
FIG. 11 illustrates another embodiment.

In addition, the period of blood flow obstruction may be further reduced by providing a structure as shown in FIG. 11. In this case, the catheter 500 includes perfusion channels 531, 532 that extend through the catheter structure to allow blood to flow along the tissue lumen during the balloon inflation time interval and before extreme cooling has occurred to freeze off the central region. In this embodiment, the balloon may be inflated to securely position and center the assembly while blood continues to flow along the vessel. Cooling is then started. While the bypass channels 531, 532 may be expected to freeze off once the cooling injection has started, the invention also contemplates that the bypass channels may be insulated from the cooling chamber, or they may include resistive or other heating elements to maintain their temperature suitable for continued blood flow during cryoablation. Such bypass passages may also be positioned in part in or through the catheter shaft or guide wire lumen.

The invention also contemplates a catheter as described above combined with other known catheter subassemblies or accessory devices such as drug delivery, energy delivery or stent delivery elements, or structures for delivering radiation. In other embodiments the catheter may include one or more additional balloons such as a primary angioplasty balloon in addition to the blocking balloons and the cryotreatment balloon described above. In yet other embodiments of the invention, the catheter may include a supply tube for ejecting a bioactive or simply thermally conductive material in the space surrounding the cooling portion, to form a temporary frozen plug which may be left in place following withdrawal of the catheter.

Figure 12B:
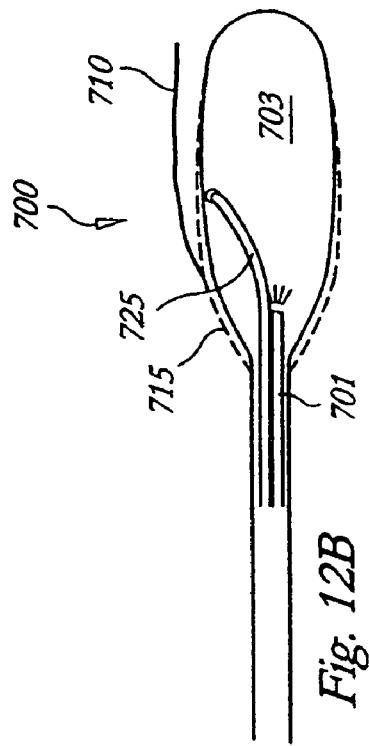
FIGS. 12A and 12B illustrate delivery embodiments.
Figure 12A:
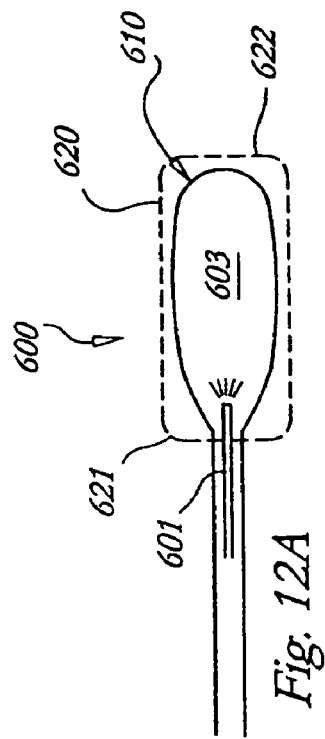

FIGS. 12A and 12B illustrate two such delivery catheters 600, 700. As shown in FIG. 12A, a first delivery catheter 600 includes an elongated body and cryogenic tip 610 with a cooling chamber 603 fed by a coolant injection lumen 601 as described above. Catheter 600 further carries a stent 620 on its outer surface and is configured to deliver and install the stent at an endoluminal site. By way of example the stent 620 is illustrated as having ends 621, 622 contoured to retain the stent on the catheter during delivery, but other retention means, such as a removable or telescoping retaining sheath may be employed. The stent is made of a shape-memory alloy or other biphasic temperature-dependent material that changes its shape when brought to predetermined temperature. For operation, the catheter tip is deployed to a desired site and then operated to bring about a temperature-dependent change in shape or dimension of the stent 620. This may be accomplished before, during, after, or independently of, the cryogenic treatment of nearby tissue. Depending on the particular alloy employed in stent 620, the fixation in position and shape change may be effected by applying cryogenic temperature, or else a mild amount of cooling may be applied to cause the stent to retain a compact shape during insertion and the stent may subsequently deploy as the surrounding temperature rises to normal body temperature. It will be understood that in general the alloy properties of such materials may be adjusted so that a relatively large change in shape or conformation is achieved at one temperature threshold, which may be above or below body temperature. Accordingly, for this aspect of the invention, applicant contemplates the possibility of providing a heater as well as the cryochamber 603 to provide both hypo- and hyperthermal conditions to carry out stent deployment.

FIG. 12B illustrates another embodiment 700 of a cryogenic delivery catheter of the invention. This embodiment again has the basic structure of a cooling chamber 703 in a distal cooling tip 710 fed by a coolant supply lumen 701. However, in this embodiment an additional fluid delivery line 725 extends through the catheter body and is mounted to deliver fluid F externally of the tip 710 into the space between the cooling chamber exterior wall and the surrounding tissue. The delivery line 725 may have one or more outlets positioned to provide fluid F in defined locations. As illustrated in phantom by element 715, a perforated membrane or other external distribution structure may also be provided to disperse or spread the fluid F exiting the delivery line 725. In general, the delivery line 725 may deliver a therapeutic treatment liquid, or simply a heat conduction fluid to cryochamber surface. Applicant contemplates generally that during cryotreatment, the fluid F will freeze in place, forming a plug that blocks flow, conducts thermal energy, and otherwise cooperates with the cryotreatment operation as described above. Advantageously, however, upon (or even prior to) completion of the freezing treatment, the catheter 700 may be withdrawn while leaving the frozen fluid mass in place. This mass then continues to chill the lumenal tissue wall, while (in the case of a vessel) circulation is immediately restored through the center. Thus, the duration of catheter freezing operation or the duration of blood flow occlusion may each be reduced, offering significant clinical advantages.

FIG. 13 illustrates yet another embodiment of the present invention, a dual balloon catheter system labeled generally as 800. Catheter system 800 includes a catheter 805, a handle unit 810, a guidewire port 815, a guidewire tube 820 enclosing a guidewire lumen 822, a coolant port 825, a coolant injection tube 830 enclosing a coolant injection lumen 835, a vacuum port 840, a vacuum return tube 845, a primary vacuum return lumen 850, a secondary vacuum return lumen 855, an inner balloon 860, an outer balloon 865, a cooling chamber 870, a proximal thermocouple 875, a distal thermocouple 880, and a distal tip 883. The thermocouples may also be coupled to a temperature gauge 885 coupled to handle unit 810.

The catheter 805 includes an elongate tube or series of tubes, conduits, flexible or rigid members generally suited for the flow of coolant therein, and for the insertion of such catheter into narrow body lumens such as blood vessels. Each of these tubes, conduits or members may include a number of lumens. As used herein, the term lumen refers not merely to the bore of a tube, but refers generally to a defined fluid pathway, suitable for the flow of coolant therethrough, connecting two or more spaces or elements such that the spaces or elements are in fluid communication. The catheter 805 is constructed similar to those embodiments previously discussed herein, and operates in a similar fashion so as to enable cryotreatment of tissue.

As shown in FIG. 13, the catheter 805 is coupled to a handle unit 810 at its proximal end, and both of balloons 860 and 865 at its distal end. The handle unit 810 is fitted with multiple ports, including a guidewire port 815 for the insertion of a guidewire (not shown) into guidewire tube 820. In addition, the handle unit 810 includes a coolant port 825 for the injection of coolant from a coolant supply (not shown) into coolant injection lumen 835. The coolant injection lumen 835 is disposed between the coaxial coolant injection tube 830 disposed around guidewire tube 820, as illustrated in FIG. 13.

A vacuum port 840 is also coupled to the handle unit 810, such port being coupled to a suitable vacuum generating device. A vacuum return tube 845 is disposed coaxially around the coolant injection tube 830 and inside of the catheter tube 805. This creates two separate coaxial vacuum return lumens: a primary vacuum return lumen 850 disposed between coolant injection tube 830 and vacuum return tube 845, and a secondary vacuum return lumen 855 disposed between the vacuum return tube 845 and the catheter body 805.

FIG. 13A illustrates a cross-section taken in the transverse direction of the catheter 805, along lines A-A in FIG. 13, showing the coaxial arrangement of the various tubes and lumens discussed above.

Turning back to FIG. 13, the catheter 805 is coupled at its distal end to two balloons, inner balloon 860, and outer balloon 865. Each of these balloons include materials and are constructed in a manner similar to those balloons discussed in previous embodiments. The inner balloon 860 has an open proximal end coupled to the coaxial return tube 845, and may have its lateral outer surface adhesively coupled to the guidewire tube 820. The outer balloon 865 is disposed around the inner balloon 860, having its proximal end coupled to the catheter tube 805 and its distal end coupled to the distal tip 883 disposed around the distal end portion of the guidewire lumen 822.

High pressure coolant is injected through the coolant port 825 into the coolant injection lumen 835, whereby it flows through such lumen to be injected into the inner balloon 860. The inner balloon 860 thereby expands to create a cooling chamber 870 therein. The coolant then flows out of the cooling chamber 870 into the primary vacuum return lumen 850, and eventually out of the device through the vacuum port 840. For purposes of this invention, a "vacuum" is merely the effect of fluid evacuation, wherein static pressure in a space may be below that of atmospheric, or may be below the static pressure in the flow region immediately "upstream" of such space. Therefore, a "vacuum", as used herein, may refer simply to the existence of a negative pressure gradient in a flow region. Thus, the flow of coolant from the cooling chamber 870 through the primary vacuum return lumen 850 is driven by the negative pressure gradient created when the pressure therein is lower than the static pressure of coolant in the chamber 870.

While the coolant is flowing through the chamber 870, two thermocouples disposed therein may take temperature readings of the coolant, such temperature being measured by the temperature gauge 885. While the proximal thermocouple 875 takes a temperature reading in the proximal section of the cooling chamber 870, a distal thermocouple 880 takes a reading of coolant temperature in the distal section of cooling chamber 870. As coolant is injected into the inner balloon 860, the flow of coolant in such balloon is non-uniform, unsteady, and turbulent, such that a uniform temperature profile for cryotreatment is not achieved for a finite time. The thermocouples 875 and 880 provide for feedback control of the flow of coolant, and of the resultant temperature profile achieved in chamber 870, thereby enabling more efficient cryotreatment.

FIG. 14 illustrates the distal end portion of the catheter system 800 of FIG. 13. In addition to the elements displayed in FIG. 13, FIG. 14 illustrates a coaxial coolant injection orifice 905, an interstitial, "intra-balloon" space 910 disposed between inner balloon 860 and outer balloon 865, and coolant flow lines F. Upon flowing through the coaxial injection tube 830, coolant enters the chamber 870 through the injection orifice 905 located in the distal half of inner balloon 860. Coolant thereafter generally flows in the direction F until the inner balloon 860 is inflated to form the cooling chamber 870 in substantially the shape and form shown in FIG. 14. Coolant then flows out of the chamber 870 through the primary vacuum return lumen 850.

While coolant is contained in the chamber 870, the flow therein is regulated by the use of thermocouples 875 and 880, so as to control the temperature profile therein. The pressure conditions inside of the chamber 870 may be regulated by controllably injecting the coolant through the orifice 905, such that the desired mixture of liquid and gas phase coolant is evaporated and expanded, respectively, inside the chamber to achieve the desired cooling power. The injected coolant may be (i) substantially in gas phase immediately upon injection, thereby using mainly Joule-Thomson cooling to lower the temperature profile in the chamber 870, or, (ii) substantially in liquid form, allowing for better control of temperature across the length of chamber 870, while still providing cooling through the endothermic boiling of liquid phase coolant.

In either case, the pressure inside of the chamber 870 must be maintained at safe levels for insertion of the device into the human body. Generally, the static pressure of coolant inside of the chamber 870 must be maintained below 15 psia, or only slightly above the ambient pressure outside of the device. If a leak or rupture through the inner balloon 860 develops, the vacuum applied through the secondary vacuum return lumen 855 will act to siphon any leaking coolant from space 910 into the vacuum return lumen 855. In this sense, the dual balloon configuration is robust with respect to balloon integrity failure, in that the failure of one balloon 860 is contained by the presence of another outer balloon 865.

Furthermore, the presence of the space 910 provides additional thermal insulation which may be necessary when operating the device at relatively low pressure inside of chamber 870. Empirical evidence shows that at chamber static pressures of 15 psia, the cooling power of the coolant flow expanding in the chamber 870 may at times be too high for safe and effective cryotreatment of adjacent tissue. In order to operate at such pressures, additional thermal resistance is needed around the inner balloon 860 to mitigate the excessive cooling power of the device. The space 910 effectively provides such insulation, which may be fine-tuned by applying varying levels of vacuum through the return lumen 855. In such a manner, the effective temperature applied during cryotreatment of tissue may be warmer than that of the boiling temperature of the coolant.

However, FIG. 14 illustrates the disposition of the outer balloon 865 around the inner balloon 860 such that an interstitial envelope or space 910 exists therebetween, when inner balloon 860 is inflated to a pressure higher than that present in the secondary vacuum return lumen 855 and hence inside of the space 910. This may be the case prior to the creation of vacuum pressure inside of the space 910, as applied through the secondary vacuum return lumen 855. However, once vacuum pressure is applied into the space 910, the balloon configuration is that shown in FIG. 15. Under such conditions, the space 910 is effectively of zero dimension along the lateral faces L of both balloons, such that the inner balloon 860 and the outer balloon 865 are in contact with one another along length L.

If the space 910 is thereby closed, the containment and insulating functions of the device are decreased. To counteract this, various methods and devices may be used to maintain the space 910 so as to enable vacuum containment of coolant leaks from, and provide additional thermal resistance around, the chamber 870, while preventing the two balloons 860 and 865 from sealing in and apposing against eachother as shown in FIG. 15. The balloons 860 and 865 may still remain in apposition versus one another, but the space 910 will be maintained to achieve one of the purposes and functions of the present invention, as more specifically explained below.

One such embodiment is shown in FIG. 16A, where the outer surface of inner balloon 860 is modified to create small surface patterns that extend from the outer surface as shown. As used herein, the term "surface modification" shall mean the creation or use of elements whose surfaces are topographically non-uniform, i.e. non-smooth. The slope at any point on such a surface may be continuous or non-continuous, but the surface itself will be continuous. These surface modifications 1010 may be achieved through conventional plasma treatment, vapor deposition, or through the use of electrically conductive or radiopaque materials as is known in the art, and may be patterned or non-patterned, so as to allow for more effective fluid pathways through the space 910. Such surface modification thereby effectively maintains the space 910 at a finite level while vacuum is applied through the return lumen 855.

Other configurations which maintain the space 910 are shown in FIGS. 16B through 16E. FIG. 16B shows the use of small particles 1020, such as talcum powder, to be lodged in the space 910. Alternatively, the space 910 could be filled with a fluid, which may itself be radiopaque or electrically conductive. In either case, the use of a vacuum return lumen coupled to the outer balloon 865 is not needed, and the outer balloon 865 is sealed to the coaxial vacuum return tube 845 which also serves as the outermost tube of the catheter shaft. This allows the particles 1020, or fluid if fluid is used, to be sealed and contained in the space 1020 during operation of the device. Alternatively, a vacuum return tube such as is used in previous discussed embodiments may be coupled to the proximal end of balloon 865 and coupled with a separate injection mechanism (not shown) for maintaining the steady flow and presence of particles 1020, or fluid, as needed, so as to maintain space 910 in its desired dimension.

FIG. 16C shows the use of regular or irregularly patterned surface ridges 1030 coupled to either of: (i) the outer surface of inner balloon 860, or (ii) the inner surface of outer balloon 865. Another alternative to maintain space 910 is to use a braid or mesh type structure 1040 as shown in FIG. 16D, wherein the mesh 1040 surrounds the outer surface of the inner balloon 860. The cross-sectional thickness of the mesh 1040 provides for the thickness of the space 910. The mesh 1040 may be a braid formed by a first group of flexible elongate elements 1042 helically wound in a first direction of rotation and a second group of flexible elements 1044 helically wound in a second direction of rotation to create a braid as shown in FIG. 16D. The space 910 is thus maintained by the apposition of each of the inner balloon 860 and the outer balloon 865 against the mesh 1040, wherein each flexible elongate element has a circular cross section defined by a diameter. In an exemplary embodiment, this diameter is in a range of approximately 0.001 to 0.010 inches. The flexible elongate elements 1042 and 1044 may be formed of metal, or a filament or fiber such as nylon, aramid, or polyester.

Finally, another embodiment uses a coil 1050 as shown in FIG. 16E. Either of the coil or mesh may be made of metal, nylon, polyimide or other suitable material, as is known in the art. The coil 1050 may include a single element wound in a direction around the inner balloon 860, or may be formed by a number of such elements wound in a parallel rotational direction so as to form a coil or spring. Each such coil element 1050 has a circular cross section defined by a diameter, wherein, in an exemplary embodiment, the diameter is in a range of approximately 0.001 to 0.010 inches. Alternatively, the coil element 1050 may have a rectangular cross section defined by a height vs. a width, wherein, in an exemplary embodiment, the height is in a range of approximately 0.001 to 0.010 inches, and the width is in a range of approximately 0.001 to 0.010 inches. The coil element 1050 may be formed of metal, or a filament or fiber such as nylon, aramid, or polyester.

The pressure conditions inside of the chamber 870 may also be monitored and regulated through the use of a pressure transducer 1060 located inside of the chamber 870, as shown in FIG. 17. The pressure transducer 1060 gives a user feedback control of the flow and pressure inside of the inner balloon 860 as the balloon is inflated and the catheter device is inserted and operated inside of a body lumen. Furthermore, the primary vacuum return lumen 850 may be set with a back pressure effective for inflating the cooling chamber 870 with the cooling fluid such that the cooling chamber 870 expands within a body lumen or vessel to position the device proximate to the vessel wall for performing cryotreatment. The back pressure is set to adjust the boiling temperature of the coolant and thereby determine the temperature applied to the surrounding tissue for cryotreatment. Such back pressure may be monitored and controlled by means of additional pressure transducers (not shown) in the catheter body. Furthermore, such a back pressure may be created by restricting the coolant return path through primary vacuum return lumen 850. Such restriction may be created by selecting a diameter of either of the injection tube 830, or coaxial return tube 845, such that the coolant flow generates a residual pressure. Alternatively, the pressure conditions, including the chamber 870 pressure and the back pressure in return lumen 850, may be regulated by the control of the coolant fluid flow rates.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of treating tissue through cooling, comprising:
   disposing a cooling device proximate the tissue, the device having a distal end portion including a primary expandable member enveloped by a secondary expandable member to define an interstitial space therebetween, the primary expandable member being in fluid communication with first and second lumens, the interstitial space being in fluid communication with a third lumen, wherein the second and third lumens are in fluid communication with one another at a proximal portion of the device;
   injecting a cooling fluid into the primary expandable member through the first lumen;
   expanding the cooling fluid inside the primary expandable member to cool the tissue;
   expelling the cooling fluid from the primary expandable member through the second lumen; and
   applying a source of vacuum to the third lumen.

2. The method of claim 1, further comprising:
   setting a back pressure in the second lumen to control the expanding of the cooling fluid in the primary expandable member.

3. The method of claim 2, further comprising:
   restricting the expelling of the cooling fluid from the primary expandable member into the second lumen to generate the back pressure.

4. The method of claim 1, wherein the cooling device further includes a pressure transducer in the primary expandable member, further comprising:
   monitoring a pressure condition in the primary expandable member.

5. The method of claim 4, further comprising:
   setting a back pressure in the second lumen in response to a pressure condition in the primary expandable member.

6. The method of claim 5, further comprising:
   restricting the expelling of the cooling fluid from the primary expandable member into the second lumen to generate the back pressure.

7. The method of claim 1, further comprising:
   upon a breach of the primary expandable member, expelling the cooling fluid from the primary expandable member through the third lumen.

8. The method according to claim 1, further comprising injecting particles into the interstitial space through the third lumen.

9. The method according to claim 1, further comprising injecting a fluid into the interstitial space through the third lumen.

10. The method of claim 1, further comprising:
    maintaining the interstitial space between the primary and secondary expandable members.

11. The method according to claim 10, wherein maintaining the interstitial space includes providing a mesh structure at least partially surrounding a portion of the primary expandable member.

12. The method according to claim 11, wherein the mesh structure includes a plurality of helically wound flexible elements.

13. The method according to claim 12, wherein at least one of the plurality of helically wound flexible elements defines a circular cross-section.

14. The method according to claim 10, wherein maintaining the interstitial space includes providing a surface modification of at least a portion of the primary expandable member.

15. The method according to claim 10, wherein maintaining the interstitial space includes providing a coil element positioned about at least a portion of the primary expandable member.

* * * * *

UNITED STATES PATENT AND TRADEMARK OFFICE
CERTIFICATE OF CORRECTION

PATENT NO. : 7,648,497 B2  Page 1 of 1
APPLICATION NO. : 11/244710
DATED : January 19, 2010
INVENTOR(S) : Lane et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 933 days.

Signed and Sealed this

Twenty-third Day of November, 2010

David J. Kappos
*Director of the United States Patent and Trademark Office*